(12) United States Patent
Kraemer et al.

(10) Patent No.: US 8,571,641 B2
(45) Date of Patent: Oct. 29, 2013

(54) APPARATUS AND METHOD FOR PROCESSING PHYSIOLOGICAL MEASUREMENT VALUES

(75) Inventors: Thomas Kraemer, Nuremberg (DE); Michael Lippert, Ansbach (DE); Olaf Skerl, Bad Doberan (DE); Gerald Czygan, Buckenhof (DE); Stefan Paule, Drosendorf (DE)

(73) Assignee: Biotronik CRM Patent AG, Baar (CH)

( * ) Notice: Subject to any disclaimer, the term of this patent is extended or adjusted under 35 U.S.C. 154(b) by 735 days.

(21) Appl. No.: 12/757,307

(22) Filed: Apr. 9, 2010

(65) Prior Publication Data

US 2010/0268041 A1 Oct. 21, 2010

(30) Foreign Application Priority Data

Apr. 15, 2009 (DE) .......................... 10 2009 002 399

(51) Int. Cl.
*A61B 5/04* (2006.01)

(52) U.S. Cl.
USPC .......................................................... 600/513

(58) Field of Classification Search
USPC .......................................................... 600/513
See application file for complete search history.

(56) References Cited

U.S. PATENT DOCUMENTS

| | | | |
|---|---|---|---|
| 5,092,343 A | 3/1992 | Spitzer et al. | |
| 5,876,353 A | 3/1999 | Riff | |
| 5,957,861 A | 9/1999 | Combs et al. | |
| 6,076,015 A | 6/2000 | Hartley et al. | |
| 6,449,509 B1 | 9/2002 | Park et al. | |
| 6,454,719 B1 | 9/2002 | Greenhut | |
| 2003/0074029 A1 | 4/2003 | Deno et al. | |
| 2003/0117296 A1 | 6/2003 | Seely | |
| 2004/0102712 A1 | 5/2004 | Belalcazar et al. | |
| 2005/0043644 A1 | 2/2005 | Stahmann et al. | |
| 2005/0240087 A1 | 10/2005 | Keenan et al. | |
| 2006/0041280 A1 | 2/2006 | Stahmann et al. | |
| 2006/0241513 A1 | 10/2006 | Hatlestad et al. | |
| 2006/0258952 A1 | 11/2006 | Stahmann et al. | |
| 2006/0264776 A1 | 11/2006 | Stahmann et al. | |
| 2006/0293609 A1* | 12/2006 | Stahmann et al. ............ 600/547 |
| 2008/0242955 A1 | 10/2008 | Uutela et al. | |

FOREIGN PATENT DOCUMENTS

| | | |
|---|---|---|
| DE | 698 26 012 | 1/1998 |
| DE | 699 26 347 | 2/1999 |
| DE | 103 61 143 | 12/2003 |

(Continued)

OTHER PUBLICATIONS

German Search Report for priority application, dated Feb. 8, 2010, 5 pages.

Yu C.M. et al. "Intrathoracic impedance monitoring in p atients with heart failure: correlation with fluid Status and feasibility or early warning preceding hosptalization". . . .

Zima, E. et al.: Determination of left ventricular volume changes by intracardiac conductance using a biventricular electrode 20 configuration. Intracardiac Impedance . . . .

(Continued)

*Primary Examiner* — Christopher D Koharski
*Assistant Examiner* — Michael Carey
(74) *Attorney, Agent, or Firm* — ARC IP Law, PC; Joseph J. Mayo

(57) ABSTRACT

A monitoring apparatus having a signal input for signals representing measurement values of one or more physiological parameters, and an evaluation and processing unit connected to the signal input. The evaluation and processing unit is designed to select, or differently weight, individual values from the values received for further processing based on one or more criteria such that measurement values raising doubts as to the validity thereof are not selected or given a very low weighting.

15 Claims, 10 Drawing Sheets

(56) References Cited

FOREIGN PATENT DOCUMENTS

| | | |
|---|---|---|
| EP | 0985429 | 9/1999 |
| EP | 1177764 | 7/2001 |
| EP | 1510173 | 6/2004 |
| EP | 1665983 | 9/2005 |
| EP | 2030649 | 7/2008 |
| WO | WO 99/43385 | 9/1999 |

OTHER PUBLICATIONS

Zipes, D.P. et al. [ed.]: Braunwald's Heart Disease; Elsevier, 2005.
Stahl, C., et al. "Intracardiac Impedance Monitors Hemodynamic Deterioration in a Chronic Heart Failure Pig Model." J. Cardiovasc. Electrophysiol. 18 (2007): 985-90.
European Search Report for priority application, dated Jun. 16, 2010, 7 pages.

* cited by examiner

APPARATUS AND METHOD FOR PROCESSING PHYSIOLOGICAL MEASUREMENT VALUES

This application takes priority from German Patent Application DE 10 2009 002 399.2, filed 15 Apr. 2009, the specification of which is hereby incorporated herein by reference.

BACKGROUND OF THE INVENTION

1. Field of the Invention

Embodiments of the invention relate to an apparatus and to a method for evaluating sensor measurement values intended to be used for predicting decompensation. In this context, the sensor measurement values refer to the output signals of sensors for physiological parameters.

2. Description of the Related Art

Patients suffering from cardiac insufficiency can, at irregular intervals, experience an acute deterioration of the state of health, associated with a complete breakdown of the body's performance, shortness of breath, and fear of suffocation. In this case, immediate hospitalization with emergency care is required.

These events are caused by what is referred to as "decompensation", which is an inability of the heart to maintain adequate blood circulation. This event manifests itself several weeks in advance by an (automatically intensifying) increase in pressure in the pulmonary circulation, and associated therewith by an increased accumulation of fluid in the lung tissue, which, however, is generally not perceived in time by the patient.

The development of decompensation, associated with tremendous stress for the patient and the cardiovascular system, considerably worsens the clinical picture of cardiac insufficiency. Early detection of developing decompensation can significantly increase the life expectancy of the patient. The potential prevention of hospitalization required due to a critical condition of the patient can lower the costs of medical care.

This requires a device which generates a warning in due time before the acute phase when decompensation is developing. As a result, corresponding therapeutic measures can be initiated at an early stage and hospitalization can be prevented.

Patients suffering from heart failure are increasingly supplied with implanted defibrillators (IDC), since part of this patient group is also at increased risk for life-threatening tachyarrhythmia.

The ICDs used are designed as single-chamber or dual-chamber systems. Approximately two thirds of all patients having heart failure suffer from systolic heart failure, in which the efficiency of blood ejection is severely worsened (for example, caused by a left bundle branch block). Today, such patients are increasingly treated with an implant, which through the synchronous stimulation of the right and left ventricles restores the synchronicity of the contractions of the left and right ventricles. The patients are given what is referred to as cardiac resynchronization therapy (CRT), wherein a pacemaker or ICD is provided with separate electrodes to the right and left ventricles (by way of the coronary sinus).

A physical parameter which allows the increasing accumulation of fluid in the thorax to be determined is the transthoracic electrical impedance. If the fluid content in the lung tissue increases, the impedance measured decreases. By using an implant and the implanted electrodes, this transthoracic impedance is easy to measure. In this way, decompensation can be detected at an early stage, prior to the acute phase, and the patient or physician can be issued a warning so as to initiate therapeutic measures.

Apparatuses measuring the transthoracic impedance between the implant housing and/or one or more cardiac electrodes in order to detect fluid accumulation in the lungs are known (U.S. Pat. No. 5,957,861, U.S. Pat. No. 6,076,015, U.S. Pat. No. 6,454,719, US 2006/0041280, US 2006/0258952, US 2006/0264776). In general, the impedance values are averaged over an extended period of time (such as over 24 hours) in order to compensate for the impedance variations caused by the cardiac and respiratory cycles and by circadian fluctuations. These averaged values serve as a basis for the early detection of developing pulmonary edemas; refer to Yu C M, Wang L, Chau E, Chan R H, Kong S L, Tang M O, Christensen J, Stadler R W, Lau C P. "Intrathoracic impedance monitoring in patients with heart failure: correlation with fluid status and feasibility of early warning preceding hospitalization." Circulation 2005; 112 (6):841-8.

Secondary effects, which are not the result of the development of pulmonary edema, can likewise strongly influence the transthoracic impedance and simulate a fluid build-up, or hide it. These interferences must be compensated for with respect to the influence thereof on the detection of developing pulmonary edema.

One of these interferences can be caused by fluctuations in the blood resistivity, which may be due to a changed hematocrit level or the varying electrolyte content in the blood, for example.

In order to reduce the influence of blood resistivity, systems are described which determine the blood resistivity and use it to correct the transthoracic impedance (US 2006/0041280, US 2006/0258952, US 2006/0264776).

The impedances of pulmonary tissue and of blood exhibit different frequency characteristics. A system has been described which, for this reason, carries out the impedance measurement at different frequencies in order to minimize the influence of the blood resistivity (EP 1 665 983).

In addition, changes in the body position (such as getting up or lying down) result in a redistribution of the fluid in the body and therefore in a temporary change in the fluid content of the lungs. These changes in the fluid content are reflected in the transthoracic impedance due to the functional principle thereof and can potentially be interpreted as developing pulmonary edema. For this reason, systems have been described which detect the body position, or the change thereof, and include it in the assessment of the transthoracic impedance (US 2006/0041280, US 2006/0258952, US 2006/0264776). Additional interference can be created by fluid accumulations in the implant pocket or due to migration of the implant.

All these solutions have the disadvantage that additional sensors or additional measurements are required. The energy required for this can significantly reduce the service life, particularly in the case of long-term implants.

Also disclosed were systems which monitor respiration directly, so as to deduce a deterioration of the health condition (U.S. Pat. No. 5,876,353, U.S. Pat. No. 5,957,861, U.S. Pat. No. 6,076,015, U.S. Pat. No. 6,449,509, U.S. Pat. No. 6,454,719, US 2006/0258952) based on the respiratory rate or the respiratory rhythm that has been determined (such as shortness of breath, Cheyne-Stokes respiration, sleep apnea).

Respiration, however, is influenced only at a relatively late stage of the pulmonary edema; refer to Zipes, D. P. et al. [ed.]: Braunwald's Heart Disease; Elsevier, 2005. In addition, respiration is also influenced by a variety of other factors, such as physical strain, speaking and the general physical condition (NYHA). As a result, unequivocal early detection of pulmonary edema purely from respiration is very prone to errors. For example, the dependency of the impedance on respiration is also utilized in order to determine the respiratory minute volume, which is used to estimate the metabolic need and employed to control a frequency-adaptive pacemaker (U.S. Pat. No. 6,076,015, U.S. Pat. No. 6,449,509).

Furthermore, methods have been described which determine hemodynamic variables by way of an intracardiac impedance measurement value and from the change thereof derive a change in the condition. For this purpose, the dynamics of the heart beat is determined and fluctuations, which are caused by respiration and other influences, are eliminated, such as by averaging (Zima, E., et al. "Determination of left ventricular volume changes by intracardiac conductance using a biventricular electrode configuration." Europace 8.7 (2006): 537-44; Stahl, C., et al. "Intracardiac Impedance Monitors Hemodynamic Deterioration in a Chronic Heart Failure Pig Model." J. Cardiovasc. Electrophysiol. 18 (2007): 985-90; EP 1 510 173).

Also known are systems that combine several different parameters in order to better assess the progression of the disease and compensate for uncertainties of individual parameters (U.S. Pat. No. 5,876,353, U.S. Pat. No. 5,957,861, US 2006/0258952, US 2006/0264776).

The known solutions have a variety of disadvantages.

A crucial disadvantage of the known solutions is due to the fact that the transthoracic electrical impedance is influenced not only by the increasing fluid build-up in the lungs, but also by many other factors. Due to the influence of these secondary factors, the sensitivity and specificity of lung fluid detection are reduced. As a result, the secondary influencing factors must be compensated for by additional parameters or additional measured variables, at times also by different sensors (such as body position, intracardiac pressure sensors). Additional measurements increase the complexity and the consumption of energy. The increased energy consumption reduces the service life of the system, particularly in the case of long-term implants. The known respiration parameters are also dependent on many other factors and have little specificity taken by themselves. Again, the use of additional parameters is required.

BRIEF SUMMARY OF THE INVENTION

It is therefore the object of one or more embodiments of the invention to provide an apparatus and a method that largely eliminate the disadvantages of the prior art, are easy to implement, and in particular offer the highest sensitivity and specificity possible.

According to one or more embodiments of the invention, this object is achieved by a monitoring apparatus comprising a signal input for signals representing measurement values of one or more physiological parameters, and an evaluation and processing unit connected to the signal input. The evaluation and processing unit is designed to select, or differently weight, individual values among the values received for further processing based on one or more of the following criteria such that measurement values raising doubts as to the validity thereof are not selected or given a very low weighting, if:
  the variability (such as standard deviation or relative standard deviation) of a measurement value, which is a mean value from many different individual values, exceeds a specified particular threshold value,
  a sensor signal identifying the activity of a patient, such as a Closed Loop Stimulation rate control signal, accelerometer output value, respiratory rate, respiration depth, and/or minute volume, exceeds a specified particular threshold value,
  a signal, or several signals, indicate an unstable condition of a patient, such as ventricular tachycardia, or
  an antitachycardiac therapy is being conducted, such as antitachycardiac stimulation or delivery of a defibrillation shock.

If, based on the above criteria, the weighting of a measurement is below a specified or adaptive threshold, the evaluation thereof can be aborted to save energy, processing time, bandwidth during the data transmission, and trend memory. If according to the above criteria a weighting below a certain threshold is already expected based on other parameters prior to conducting a sensor measurement, or based on partial measurements during the measurement (such as the first minute of a 10-minute measurement), this measurement can also be entirely eliminated or aborted, for the same reasons. Aborted or eliminated measurements therefore also contribute to savings with respect to energy and/or processing time and/or data transmission and/or trend memory.

Furthermore, if according to the above criteria the weighting of a measurement were to be below a specified or adaptive threshold, a measurement can be postponed by up to a maximum delay to be established beforehand, until the criteria are again in the useful range. In this way, optionally for energy savings purposes, the completeness of a series of measurements having valid measurement points can be improved. Which method is selected, and the decision with respect to omission or postponement, will depend on the priorities assigned to energy savings and completeness of the series of measurements.

An explanation of the Closed Loop Stimulation rate control signal is provided in the description of FIG. 4.

The evaluation and processing unit is preferably designed to select, or differently weight, individual values among the values received for further processing based on one or more of the following criteria such that measurement values having high consistency of the conditions, and therefore good comparability, are given a high weighting and preferred in the evaluation.

The evaluation and processing unit, for example, is designed to give a high weighting to and preferentially evaluate measurement values which are recorded during a specified time range, such as bedtime.

In addition, or as an alternative, the evaluation and processing unit can be designed to give a high weighting to and preferentially evaluate measurement values which are associated with a specified heart rate range (such as BasicRate (BR) . . . BR+10 bpm).

The evaluation and processing unit can also be designed to give a high weighting to and preferentially evaluate measurement values which are associated with a specified stress range (such as CLS stimulation rate control signal range).

According to a further preferred embodiment, the evaluation and processing unit is designed to give a high weighting to and preferentially evaluate measurement values which accompany a fraction of atrial fibrillation within a certain time period (atrial burden), which is below or above a specified threshold value.

The evaluation and processing unit can preferably be designed to give a high weighting to and preferentially evaluate measurement values with accompany a respiratory amplitude and respiratory rate in a predetermined or adaptively determined interval.

According to a particularly preferred embodiment, the evaluation and processing unit is designed to select, or differently weight, individual values among the values received for further processing according to one or more of the following criteria such that measurement values obtained under conditions during which the measurement signal exhibits high sensitivity toward the effect to be observed are preferentially evaluated and given a higher weighting.

In this context, the evaluation and processing unit is designed to give a high weighting to and preferentially evaluate measurement values which accompany a fraction of atrial fibrillation within a certain time period (atrial burden), which is above a specified threshold value.

The monitoring apparatus preferably comprises an input for a position sensor signal, which indicates a change in the position (such as horizontal or vertical position). The evaluation and processing unit is then preferably designed to give a high weighting to and preferentially evaluate measurement values which are recorded after a change in position into a horizontal position.

The evaluation and processing unit can also be designed to give a high weighting to and preferentially evaluate measurement values which are recorded under high physical strain.

In addition, or as an alternative, the evaluation and processing unit can also be designed to give a high weighting to and preferentially evaluate measurement values which are recorded at a high heart rate.

In the case of a monitoring apparatus having an input for a position sensor signal, which indicates a horizontal or vertical position, and having an input for a time-of-day signal, the evaluation and processing unit is preferably designed to give a high weighting to and preferentially evaluate measurement values which are recorded in the morning, after switching from a horizontal position into a vertical position (which is to say, when getting up in the morning).

The evaluation and processing unit is preferably connected to an impedance capturing unit for determining an impedance signal, which represents an intracardiac impedance curve, and to an impedance evaluation unit, which determines an activity signal indicating high physical strain (CLS signal) from the time curve of the impedance signal.

According to the one or more embodiments of the invention, the object is also achieved by a method for processing measurement values of physiological parameters, wherein individual values are selected, or given different weighting, among the values received for further processing based on one or more of the following criteria such that measurement values raising doubts as to the validity thereof are not selected or given a very low weighing, if:
- the variability (such as standard deviation or relative standard deviation) of a measurement value, which is a mean value from many different individual values, exceeds a specified particular threshold value,
- a sensor signal identifying the activity of a patient, such as a Closed Loop Stimulation rate, accelerometer output value, respiratory rate, respiration depth, and/or minute volume, exceeds a specified particular threshold value,
- a signal, or several signals, indicate an unstable condition of a patient, such as ventricular tachycardia, or
- an antitachycardiac therapy is being conducted (ATP, shock).

BRIEF DESCRIPTION OF THE DRAWINGS

Embodiments of the invention will now be described in more detail with reference to an exemplary embodiment illustrated the figures. Shown are.

DETAILED DESCRIPTION OF THE INVENTION

Figure 1:
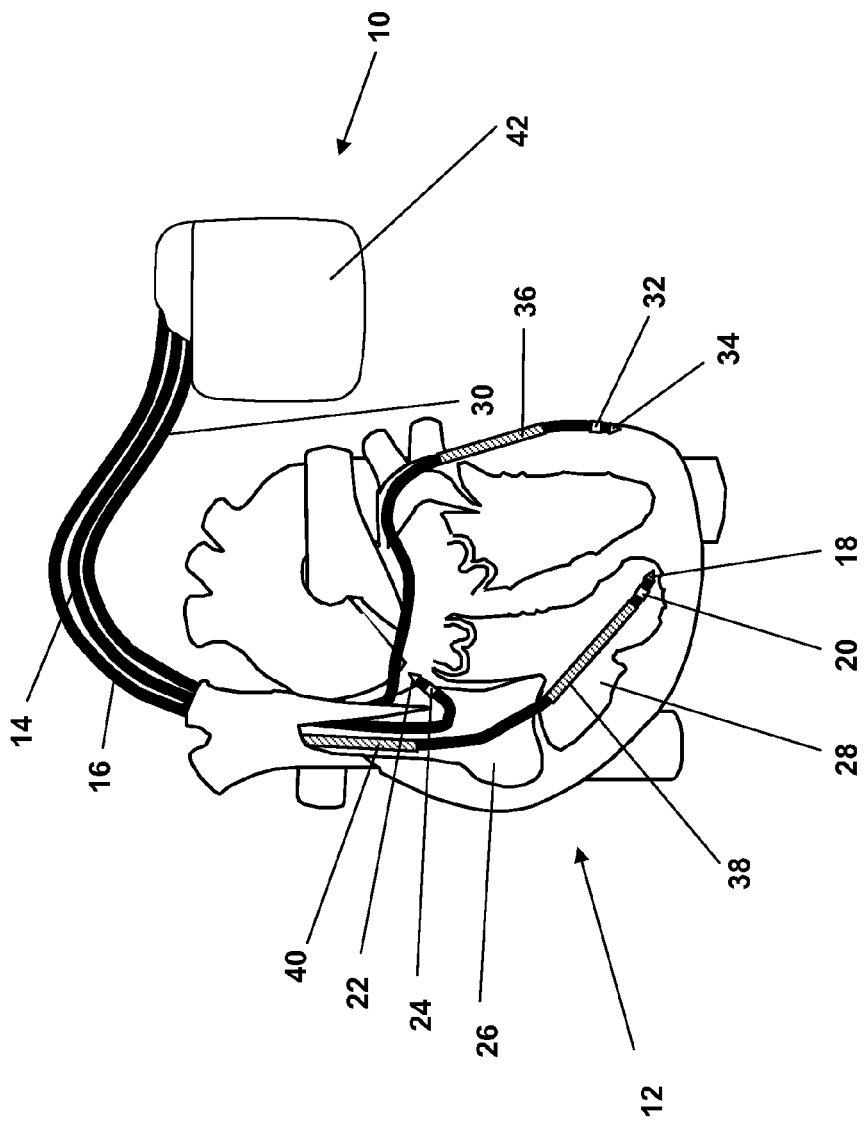
FIG. 1 an implant according to an embodiment of the invention in the outside illustration.

FIG. 1 shows an implant 10 in the form of a biventricular tri-chamber pacemaker and/or cardioverter/defibrillator (ICD). Connected to the implant are three electrode leads, which is to say a right atrial electrode lead 14, a right ventricular electrode lead 16, and a left ventricular electrode lead 30. In the implanted state, the right atrial electrode lead 14 ends in the right atrium 26 of a heart 12. The right ventricular electrode lead 16 ends in the right ventricle 28 of the heart 12, and the left ventricular electrode lead 30 extends over the coronary sinus of the heart 12 to the left ventricle of the heart.

At the distal end, the right atrial electrode lead 14 carries a right atrial tip electrode 22, and a small distance therefrom a right atrial ring electrode 24. Similarly, at the distal end, the right ventricular electrode lead 16 carries a right ventricular tip electrode 18 and slightly away therefrom a right ventricular ring electrode 20. A left ventricular tip electrode 34 and slightly away therefrom a left ventricular ring electrode 32 are also disposed at the distal end of the left ventricular electrode lead 30. These electrodes are used to receive electric potential in the respective ventricle and deliver stimulation pulses to the respective ventricle during normal pacemaker operation. This does not require a detailed explanation at this point.

In addition, the right ventricular electrode lead 16 also carries a right ventricular shock coil 38, which in the implanted state is disposed in the right ventricle, and a second shock coil 40, which in the implanted state is located in the superior vena cava. A left ventricular shock coil 36 is also provided on the left ventricular electrode lead 30. The shock coils serve, when needed, as defibrillation electrodes for delivering defibrillation shocks. This too does not require a detailed explanation at this point.

For one or more embodiments of the invention, however, it is important that the implant 10 is designed to deliver a weak subthreshold alternating current, which is to say an alternating current which does not produce tissue contractions, by way of the metal conductive housing 42 thereof and, for example, the right ventricular shock coil 38, and to measure the voltage decreasing as a result of the fed alternating current by way of the right ventricular tip electrode 18 and an opposite pole formed by the electrically conductive housing 42. In a manner which is known per se, in this way a transthoracic impedance can be determined.

Figure 2:
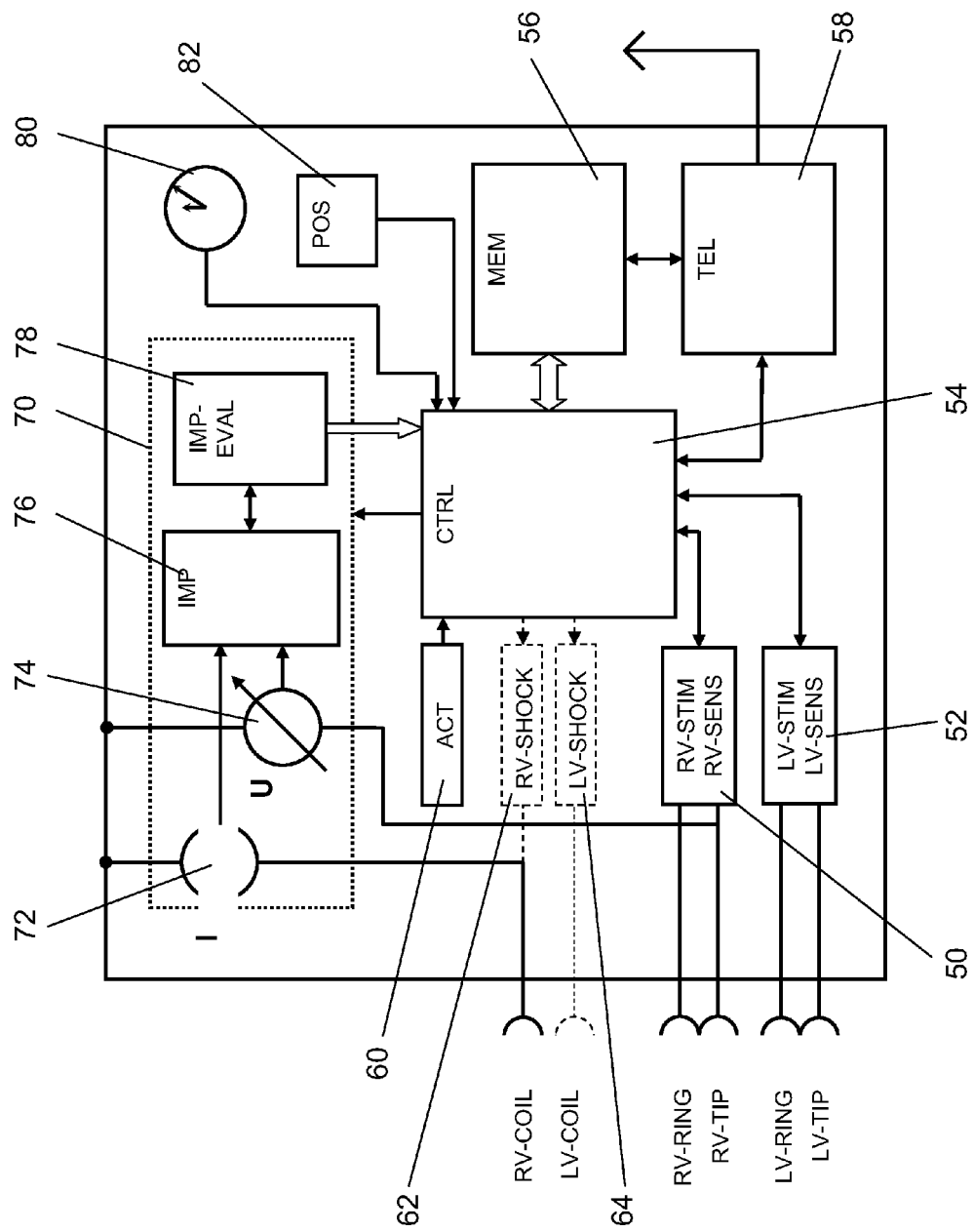
FIG. 2: a block diagram of a first embodiment of the implant according to the invention.

FIG. 2 shows a schematic block diagram of the implant 10 comprising the usual components of a pacemaker/cardioverter/defibrillator, which is to say connections for the electrode leads shown in FIG. 1, and for the electrical components connected thereto and accommodated in the hollow housing 42, such as a right ventricular defibrillation shock generator 62, a left ventricular defibrillation shock generator 64, a right ventricular sensing and stimulating unit 50 (which for the sake of simplicity in this illustration are combined into one unit), and a corresponding left ventricular stimulating and sensing unit 52. These components are connected to a central control unit 54, which additionally is connected to an activity sensor 60.

In addition, a clock 80 is provided, which supplies a time-of-day signal indicating the respective time of the day, thereby allowing a differentiation between day time and night time. A position sensor 82 is designed to derive a position signal from the position of the implant so as to be able to distinguish in this way a sitting from a standing position, which is to say a vertical position of a patient from a horizontal position.

A memory 56 is used to save program data for controlling the control unit 54 and for saving measurement values and operating parameters obtained by the implant 10. The control unit 54 and the memory 56 are furthermore connected to a telemetry unit 58, which enables the wireless transmission of data from the implant 10 to an external patient device, or conversely the receipt of data, such as new control parameters, therefrom.

Figure 3:
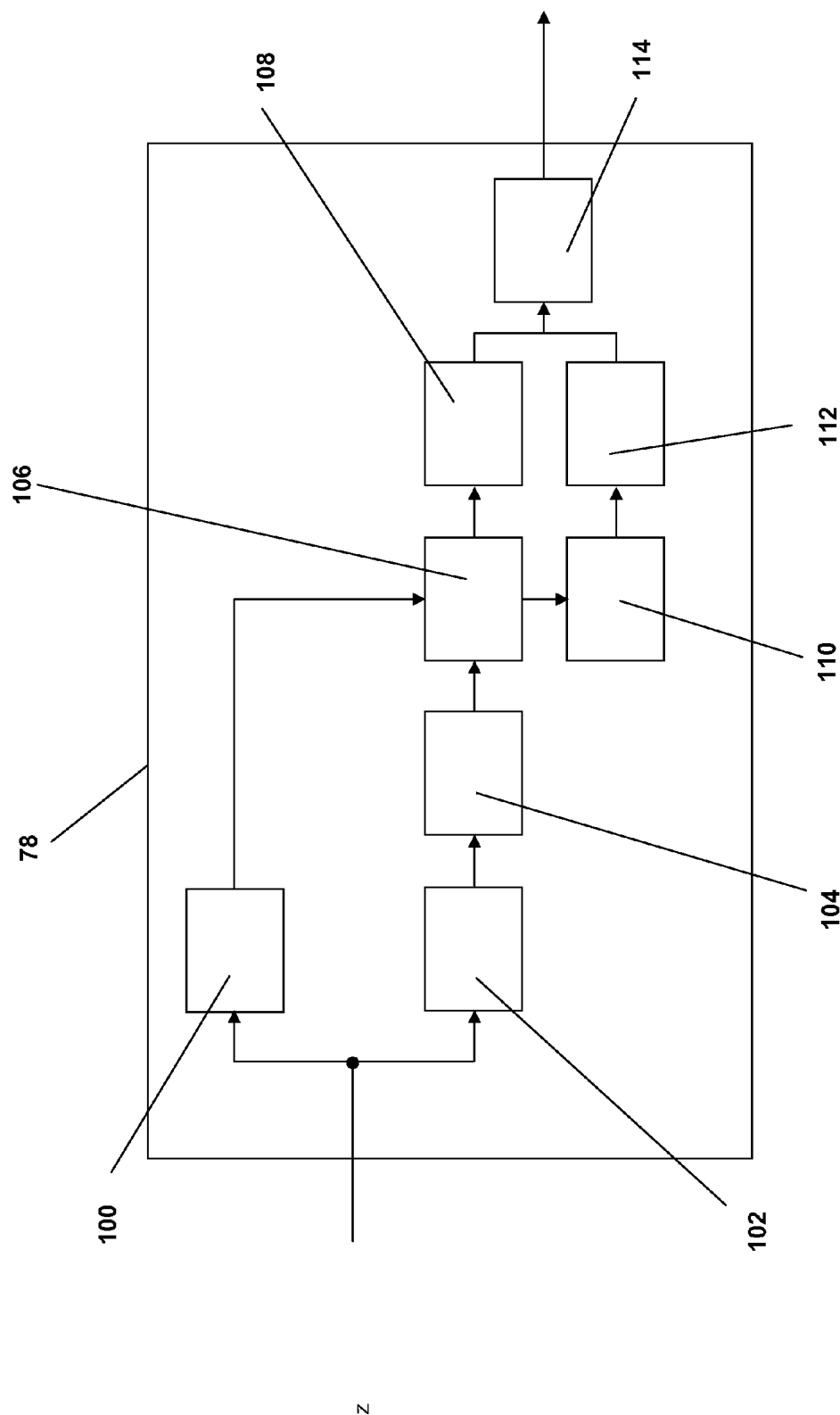
FIG. 3 a block diagram of an exemplary embodiment of an impedance evaluation unit of the implant according to the invention.

An impedance capturing and evaluation unit 70 comprises an AC power supply 72 and a voltage measuring unit 74. The AC power supply 72 is designed to generate two-phase current pulses in a manner which is known per se and to output them by way of the RV-Coil connection and the right ventricular shock coil 38, and also by way of the housing 42, to body tissue located in between in the implanted state. The voltage measuring unit 74 measures the voltage resulting from the alternating current pulses that are output. The intensity of the output current pulses and the resulting voltage are measured at regular intervals by an impedance capturing unit 76, thereby creating a chronological sequence of values representing the respective impedance, hereinafter referred to as the impedance values, which reflect the temporal curve of the impedance between the housing 42 of the implant and the right ventricle. This impedance is the transthoracic impedance. An evaluation unit 78 is provided for evaluating this impedance curve and evaluates the impedance as follows (refer to FIG. 3).

The sequence of impedance values originating in the impedance capturing unit 76 is first subjected to digital filtration in order to determine the mean value M of the impedance curve and a respiration signal R by way of digital filtration using different time constants. A first digital filter 100 is used to determine the mean value M, and a second digital filter 102 is used to determine the respiration signal R. An RMS value determination unit 104, which is used to determine the root mean square value of the respiration signal R, is connected downstream of the digital filter 102. Connected downstream thereof is a ratio determination unit 106, which is connected to the RMS value determination unit 104 by way of a first input and to the first digital filter 100 by way of a second input, and which is designed to produce the ratio between the RMS value of the respiration signal R and the mean impedance M. This ratio constitutes a modulation parameter determined by the impedance evaluation unit 78, the parameter value of which is compared to a threshold value serving as the reference value in a downstream first comparator 108.

The ratio determination unit 106 is additionally connected on the output side to a trend determination unit 110, which subtracts two consecutive modulation parameters from each other and compares this subtraction to a preceding subtraction. This comparison can also be carried out by forming the difference. The output signal obtained in this way is fed to a second comparator 112, which is used to compare this output signal to a second threshold value as the reference value.

The output values of the first comparator 108 and of the second comparator 112 are fed to an evaluation unit 114, which generates, or does not generate, a decompensation warning signal as a function of the two comparison results.

Figure 4:
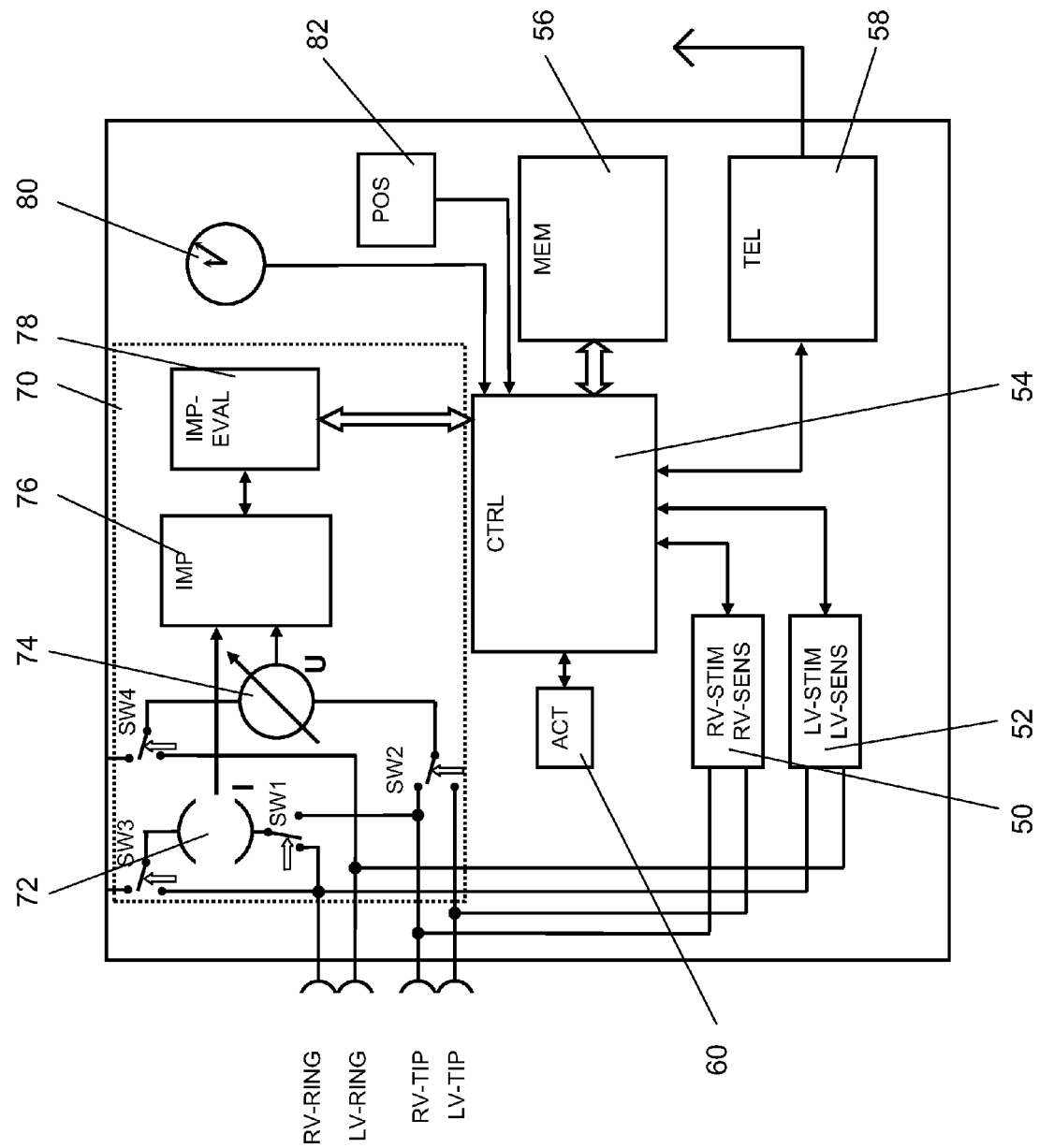
FIG. 4 a block diagram of a second embodiment of the implant according to the invention.

FIG. 4 shows an alternative embodiment of the implant 10, wherein the alternating current to be delivered to the tissue is output by way of the housing 42 of the implant, and also by way of the right ventricular ring electrode 20 and the left ventricular ring electrode 32. The voltage is measured by way of the housing 42 of the implant 10, and by way of the right ventricular tip electrode 18 and the left ventricular tip electrode 34. Further electrode configurations for measuring the transthoracic impedance are known in principle and possible.

The impedance capturing and evaluation unit 70 furthermore comprises switches SW1, SW2, SW3 and SW4, by way of which the voltage measuring unit 74 can be selectively connected to the right ventricular tip electrode 18 and to the housing 42 for determining a transthoracic impedance curve, or to the left ventricular tip electrode 34 and the left ventricular ring electrode 32 for recording an intracardiac impedance curve. In the first instance, the current is fed by way of the right ventricular ring electrode 20 and the housing 42, and in the latter case it is fed by way of the right ventricular tip electrode 18 and the right ventricular ring electrode 20. In order to capture the dynamics of ventricular contraction for determining a stimulation rate control signal within the scope of the Closed Loop Stimulation (CLS), the current is fed and the voltage is measured by way of the right ventricular tip electrode 18 and the housing 42 of the implant 10. For this purpose, a differential area is determined and evaluated between a present impedance curve and a reference resting curve.

This signal is also included in the weighting of the captured measurement values.

The detection of decompensation takes place, for example, by evaluating the temporal curve of the intrathoracic impedance $Z(t)$.

The explanations below are provided for a more profound understanding of the invention and describe further possible embodiments of the impedance evaluation unit 78, which are not illustrated in detail here.

The transthoracic impedance fluctuates temporally around a mean value M, which is to say the impedance is cyclically modulated by the cardiac motions and respiration. The time curve of the impedance $Z(t)$ is shaped by the relatively high-frequency cardiac motion, with which the slower respiration cycle R is superimposed.

Figure 5:
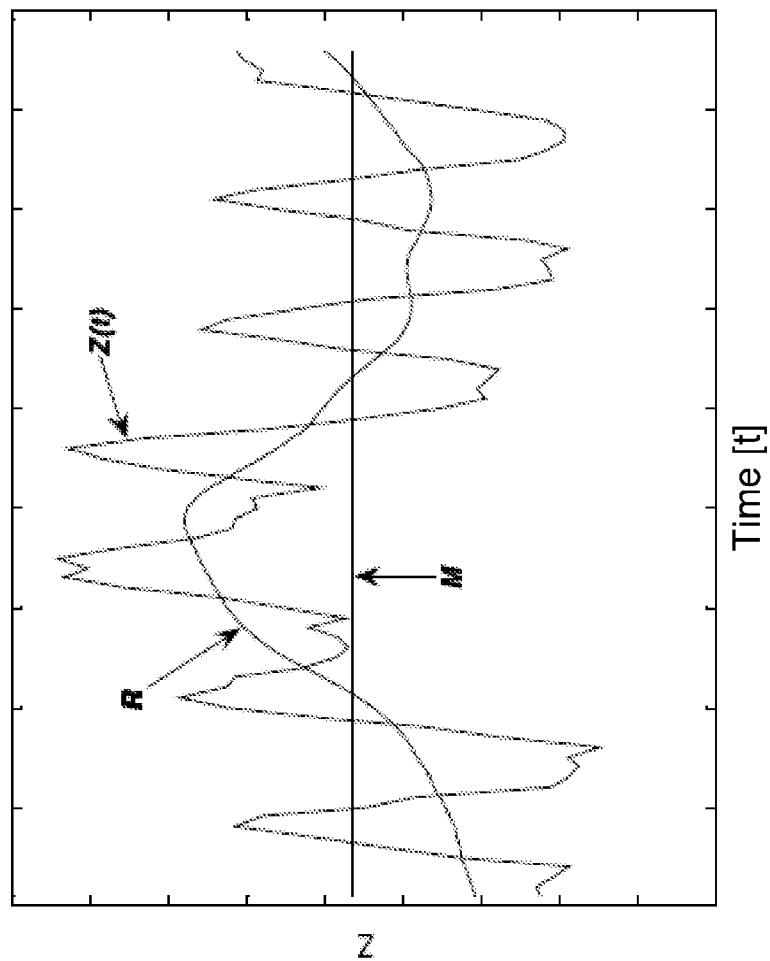
FIG. 5 an exemplary illustration of a temporal impedance curve, including the associated mean value and respiration signal.

FIG. 5 is an exemplary illustration of a time curve of the intrathoracic impedance $Z(t)$, including the associated mean value (M) and the respiration signal (R).

Figure 6:
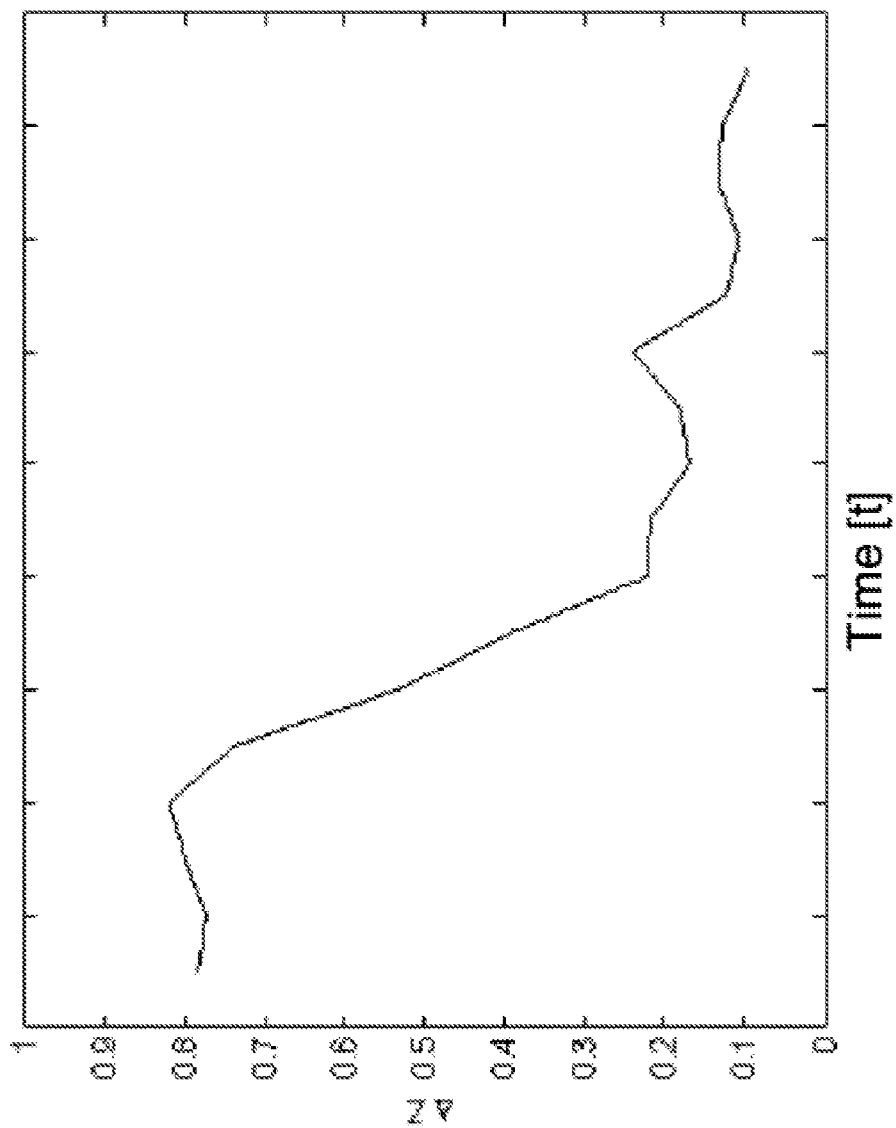
FIG. 6 a reduction in the RMS value of the respiration signal during the formation of pulmonary edema.

As the fluid accumulation in the lungs increases, the mean impedance value is known to decrease, a fact which the known pulmonary edema detection methods take advantage of. However, it was found that the modulation of the transthoracic impedance (respiration signal, R) caused by respiration likewise significantly declines, even if the respiration depth and respiratory rate remain unchanged, refer to FIG. 6

The fluid built up in the lungs increasingly short-circuits the pulmonary tissue. As a result, the influence of the changing air content in the lungs on the impedance declines during a respiration cycle. Impedance modulation is directly coupled to respiration. Other factors, such as changes in the blood resistivity, can thereby separated with respect to the influences thereof, unlike in the case of the mean impedance. Changes in the respiration modulation of the transthoracic impedance as a result of the fluid build-up in the lungs can be detected long before respiration exhibits symptoms of impairment.

In order to be able to determine meaningful parameters for the respiration modulation, the component (R) caused by respiration must be separated from the constant component of the transthoracic impedance (M) and from the component caused by the cardiac cycle (heart signal). This is done by the impedance evaluation unit. The unit can employ generally known methods for this purpose, such as different filtration methods or measurement of the impedance synchronous with cardiac cycles. These methods isolate the respiration signal R from the time curve of the transthoracic impedance Z(t). The isolated respiration signal is employed to derive suitable parameters, which describe the degree of the modulation and can be used to assess the fluid accumulation in the lungs. The impedance evaluation unit is preferably designed to determine one or more of the following modulation parameters:

RMS value or mean amplitude of the respiration signal,
ratio of the RMS value or mean amplitude to the mean impedance M,
relation of the RMS value to the respiratory rate,
interquartile range, wherein this enumeration is only exemplary in nature and is neither exhaustive nor limiting. The impedance evaluation unit then compares the value of one or more of these modulation parameters to a criterion, such as a threshold value, and decides on the detection of decompensation (if the threshold value is exceeded, for example). The criterion can be a fixed specified variable or can be set individually for the patient.

In addition, the impedance evaluation unit can also be designed to record and evaluate the trends of one or more modulation parameters over a suitable time duration. Based on these trends, the preferred impedance evaluation unit can again determine suitable trend parameters, in particular one or more of the trend parameters listed below:

the difference compared to the previous parameter value or the change of this difference compared to the previous one,
circadian fluctuations of the parameter or parameters,
changes in the circadian fluctuation of the parameter,
change in the relation between the respiration amplitude and respiratory rate.

These trend parameters are again compared by the impedance evaluation unit to a criterion, thereby detecting decompensation. Furthermore, the impedance evaluation unit can be designed to link the parameter trend to the threshold value. In this way, the impedance evaluation unit can derive an assessment of developing decompensation, for example, from the duration and the degree by which the value dropped below the threshold value.

Figure 7:
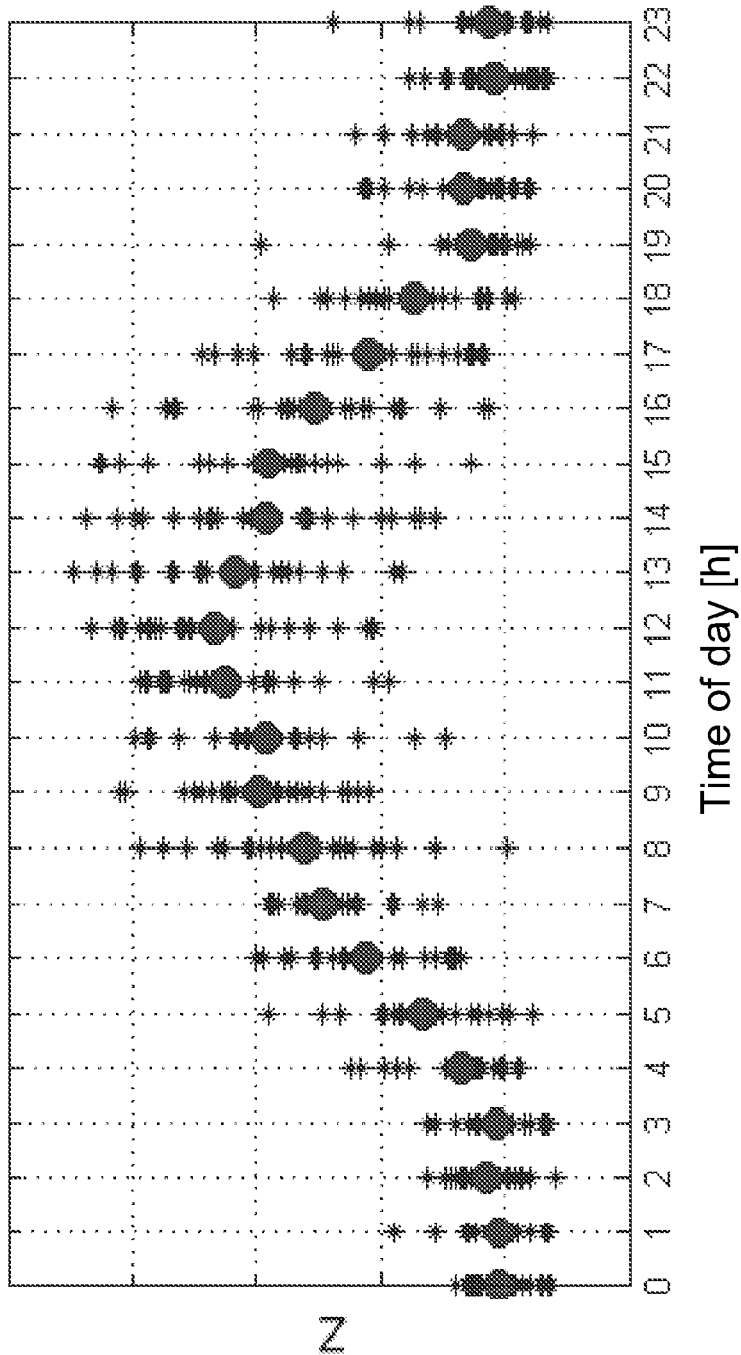
FIG. 7 the course of the trend of the average impedance.

When looking at the trend of the mean impedance M, temporal fluctuations are apparent, which indicate a clearly circadian (dependent on the time of day) rhythm of the impedance, refer to FIG. 7.

It can be assumed that the circadian pattern of the impedance can be attributed to fluid shifts in the body associated with other rhythmological (such as heart rate) and/or hemodynamic variables (such as blood pressure) as a function of the time of day. However, other, such as hormonal, influencing factors can also play a role. For this reason, the circadian pattern may be significantly determined by the state of health of the patient, because recovery phases, for example, at night are less pronounced in sick patients than in healthy or less sick patients. As a result, the circadian signal of the impedance and/or parameters derived therefrom are also used for detecting pulmonary edema and/or for evaluating the existing or progressing cardiac insufficiency.

The impedance evaluation unit is preferably designed to determine the circadian signal from the mean impedance M by using suitable methods, such as hourly averaging of the cyclically measured impedance values.

The implant, for example, conducts measurements of the intracardiac impedance at regular intervals (such as 1 hour), these measurements consisting of many individual measurements ($Z_i$), for example, an impedance measurement for 15 minutes per cardiac cycle, or for a few minutes continuously using a constant sampling frequency, such as 32 Hz. A mean value ($Zmean_h$) and a variance ($Zvar_h$) are calculated from each of the hourly measurements. These measurement values (such as n=24) are used every day to calculate a series of parameters P derived from the impedance. For each parameter, this results in one value P per day.

In the preferred embodiment, the impedance evaluation unit uses this circadian signal again to determine parameters (circadian parameters) which characterize this signal. The impedance evaluation unit is preferably designed to determine one or more of the circadian parameters mentioned below:

maximum daily fluctuation of the impedance as the difference between the maximum and minimum values,
the ratio of the durations of the two half periods (above and below the mean daily value) to each other,
phasing of the circadian fluctuation, such as the time of maximum and/or minimum,
difference of the impedance values of two constant points in time, or also the day-night difference.

According to a further preferred embodiment, the impedance evaluation unit is designed to again compare these circadian parameters to a criterion. In this way, an assessment can be derived about developing or imminent decompensation, or the development of the underlying cardiac insufficiency can be evaluated. The impedance evaluation unit can further be designed to determine the trend of one or more circadian parameters over a suitable time duration and to derive circadian trend parameters, which likewise can be compared to a criterion. In addition, the impedance evaluation unit can be designed to link the trend to the criterion in order to make an assessment of the degree of decompensation.

Furthermore, the impedance evaluation unit can be designed to link a circadian parameter, or the trend thereof, to the trend of a modulation parameter of the respiration signal, or directly to the modulation parameter, such as phase displacement between the circadian signal and circadian trend of a respiration signal parameter,
comparison of the respiration signal parameters in only a certain part of the circadian rhythm (such as always at certain times or at times of a minimum in the circadian signal).

The impedance evaluation unit can likewise be designed to evaluate the correlation between one or more parameters of the circadian signal and parameters of the respiration signal, and to derive therefrom the degree of decompensation.

Figure 8:
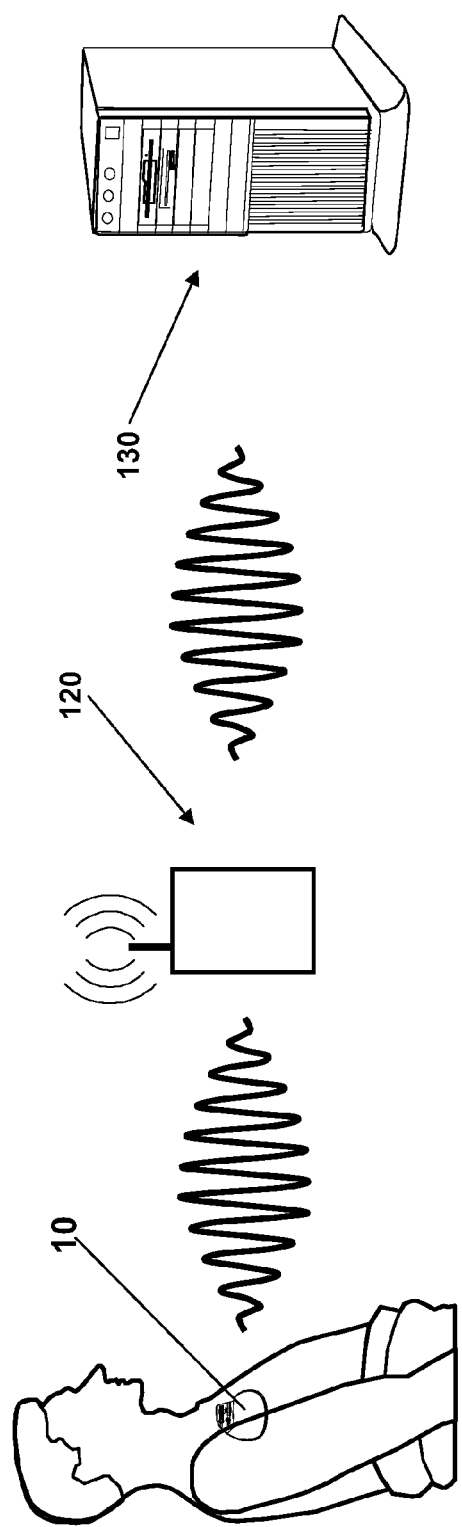
FIG. 8 an implant according to an embodiment of the invention, in conjunction with a patient device and a service center.

The determination of the parameters and trends, and the analysis compared to the corresponding criterion, can be carried out completely in the implant, if the impedance evaluation unit is completely integrated in the implant. If the impedance evaluation unit as a result of the analysis compared to the criterion detects decompensation, the implant can generate an alarm (for example, acoustically, or by vibration, or by sending an alarm message using a telemetry connection to an external patient device 120; refer to FIG. 8), or it can independently take measures for adapting the therapy, such as dispensing drugs, for example, or adapting the dosage of the drugs, or adapting the stimulation parameters in pacemakers or ICDs.

The implant can also only determine the corresponding parameters and send them to an external patient device by way of a telemetry connection. In the patient device, the trends may be determined and analyzed compared to the criterion. In this case, the impedance evaluation unit is at least part of the patient device. Upon detecting decompensation, the patient device can generate an alarm (again, for example, acoustically, or by notifying the physician or a service center by way of a data connection) or it can independently initiate therapeutic measures. The patient device can also forward the parameters by way of a data connection at suitable intervals to a service center, where the trends can be determined and the analysis compared to the criterion can be carried out. In this case, at least part of the impedance evaluation unit is part of the service center. It is also conceivable and advantageous to divide the impedance evaluation unit among the patient device for the preliminary evaluation and the service center for the trend evaluation and subsequent further evaluation. If decompensation is detected, the service center can also alarm the treating physician in a suitable manner, or make data available to the physician for a personal evaluation in a suitable manner. The implant can also only save the impedance values and send them to the patient device at suitable intervals.

The determination of the parameters and trends, and also the analysis thereof compared to the criterion, can again be carried out in the patient device or in the service center.

A possible variant (variant A) includes an ICD 10 having a defibrillation electrode 38 in the right ventricle. The transthoracic impedance measurement is conducted by feeding current via the shock coil 38 and the ICD housing 42 and by measuring the voltage by way of the right ventricular tip electrode 18 and the ICD housing 42 (refer also to FIGS. 1 and 2). In this way, a sufficiently large part of the lungs is captured by the measurement path.

In order to save energy, the impedance is measured once every hour for approximately 30 seconds using a high sampling frequency, such as 32 measurements per second. The implant uses these measurement values to determine the mean impedance M by averaging all values. Furthermore, the respiration signal is isolated from the measurement values, and the RMS value thereof is determined, by way of an appropriate digital filter. The RMS value and the mean impedance are used to calculate the relative RMS value of the respiration modulation, and the relative RMS value is saved in the internal trend memory. Once a day at a suitable fixed time, the mean daily value of the relative RMS value is calculated from the trend memory and saved in a long-term memory. If this mean daily value is higher than an established value for longer than an established time, it is considered an indicator of decompensation. To do so, for example, the difference between the present and the previous mean daily values is added into a difference sum when the mean daily value drops. If the mean daily value remains constant or rises, the difference sum is incrementally reduced again. If the difference sum exceeds an established threshold value, it is considered an indication of decompensation, and the implant triggers an alarm. It is also conceivable for the implant to send the trend memory, or the mean daily value, to an external patient device using a telemetry connection. The patient device can then calculate and evaluate the parameters and trigger an alarm, or it can forward the data to a service center, which then performs the further processing of the data.

A further possible variant (variant B) again includes an ICD 10 having a defibrillation electrode 38 in the right ventricle. The transthoracic impedance measurement is carried hourly as in variant A. The implant uses the measured impedance values to determine the mean impedance by averaging all values and determines the respiration signal using an appropriate digital filter, and calculates the RMS value.

Both values are saved in a trend memory 56. Using a telemetry connection, the trend memory content is transmitted once a day by the telemetry unit 58 to an external patient device 120, which forwards the data via an Internet connection to a service center 130, refer to FIG. 8. In the service center 130, the circadian cycles for the mean impedance and the RMS value of the respiration signal are determined. Based on these circadian cycles, suitable parameters are determined in the service center, such as the maximum daily fluctuations and the phasing between the two cycles relative to each other as the time difference between the respective maximums. Daily fluctuations and phasing are then compared to specified threshold values, which can also be specified as a function of the patient. If a threshold value, or a suitable combination of threshold values, is exceeded, also in combination with other patient data available in a database, the patient condition is rated "critical" and labeled accordingly. In addition, the treating physician can be notified in a suitable manner. The physician can then verify the state of health of the patient and optionally initiate therapeutic measures.

A further possible variant (variant C) likewise comprises an ICD 10 having transthoracic impedance measurement, as in variant A. The implant 10 again determines the mean impedance every hour, saves it to a trend memory 56, and transmits it to an external patient device 120, which forwards the data to a service center 130. In the service center, the mean daily value of the mean impedance and the circadian cycle thereof are determined. From the circadian cycle, the time durations of when the mean daily value was not met (lower half wave) and exceeded (upper half wave) are determined. The ratio of the two time durations to each other is compared to a specified threshold value, and if the value is exceeded, the condition of the patient is rated "critical" and labeled accordingly. In addition, the treating physician can be notified in a suitable manner. The physician can then verify the state of health of the patient and optionally initiate therapeutic measures.

According to one or more embodiments of the invention, the measurement values recorded as described above are weighted or discarded prior to further evaluation.

In this respect, several examples will be explained below. The selection and weighting methods described here by way of example can, of course, also be used in arbitrary other combinations:

Measurement values raising doubts as to the validity thereof can be discarded as follows:

In order to calculate $Zmean_h$ and $Zvar_h$ (see above), individual values $Z_i$ are discarded if the validity thereof raises doubts, for example, because an individual measurement exhibits a very strong deviation ("outlier") or an individual heart beat having a strongly deviating frequency (for example, during premature ventricular contraction, PVC) is present. The measurement is extended accordingly, or declared invalid, if the quantity of valid values for calculating $Zmean_h$ is insufficient.

An hourly measurement can also be omitted, postponed, or aborted as the individual measurements are being recorded if the result does not meet the validity criteria, for example, because the variability $Zvar_h$ is too high, or a value was too high for an accelerometer signal, respiration signal, CLS rate, or heart rate. An hourly measurement can also be omitted, postponed, or aborted as the individual measurements are being recorded if ventricular tachycardia is present, an antitachycardiac therapy is being conducted, or the variance of the individual measurements is too high.

A high weighting for measurements having little variance can be given as follows, for example:

According to a first example, the weighting of the mean hourly values is assigned based on the "stability" of the measurements, such as the reciprocal value of the variance. This produces a parameter $Zmean_{d\_w}$, which takes measurements under stable conditions more strongly into consideration: for example:

$$Zmean_{d\_w} = \sum_i \frac{Zmean_h(i)}{Zvar_h(i)} \bigg/ \sum_i \frac{1}{Zvar_h(i)}$$

Figure 9:
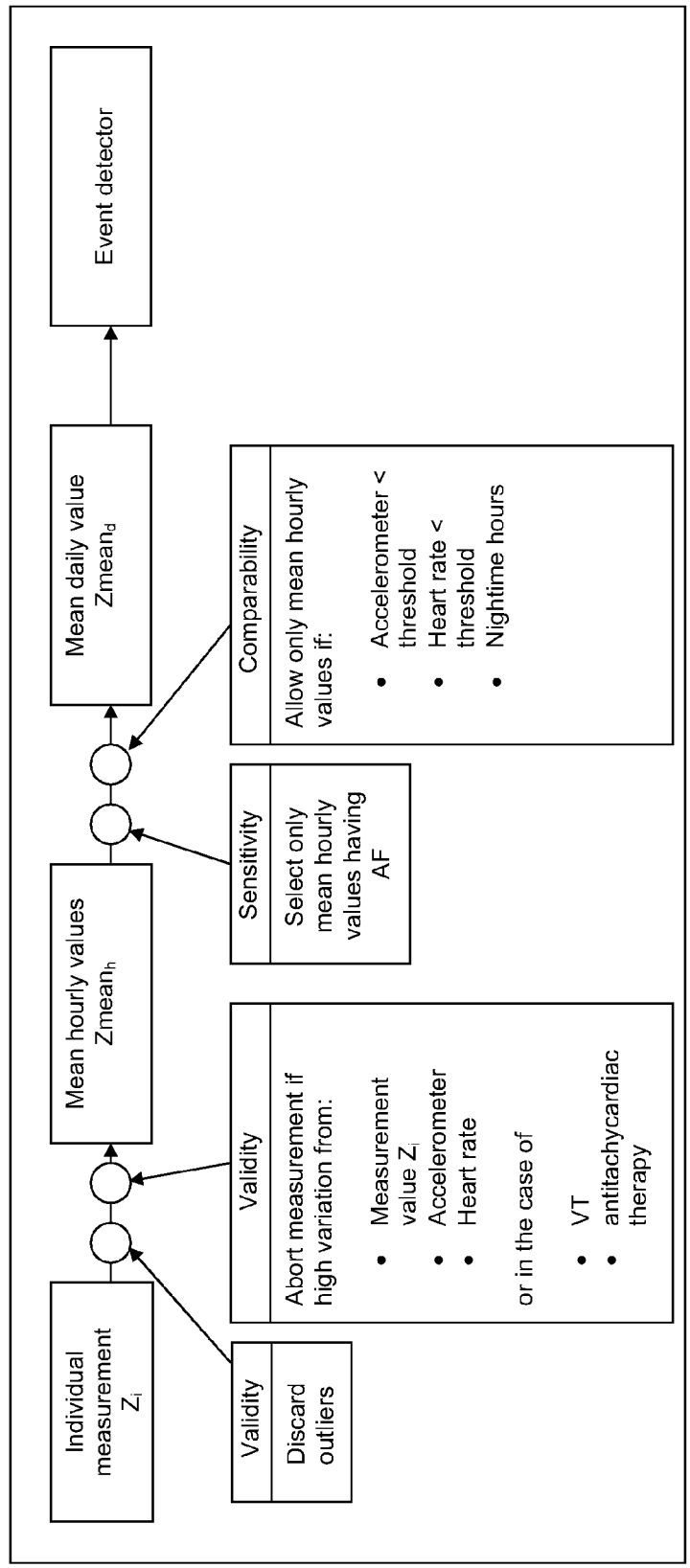
FIG. 9: an example of the selection of measurements during atrial fibrillation (AF)

A selection or a high weighting of measurements $Zmean_h$ can also take place if the impedance values are recorded under conditions which are particular sensitive to the effect to be observed. For this purpose, measurements having high comparability of the conditions are preferred. This will be explained below in more detail based on several examples:

A second example, which is illustrated in FIG. 9, relates to the selection of measurements during atrial fibrillation AF:

Measurements during AF are selected and separately averaged to form a mean daily value under AF: $Zmean_{d\_AF}$ Only the $Zmean_h$ values which meet the following additional conditions are taken into account (for comparability):
  i. Accelerometer signal below a threshold (patient at rest)
  ii. Heart rate below a threshold (patient at rest)
  iii. Night time.

Figure 10:
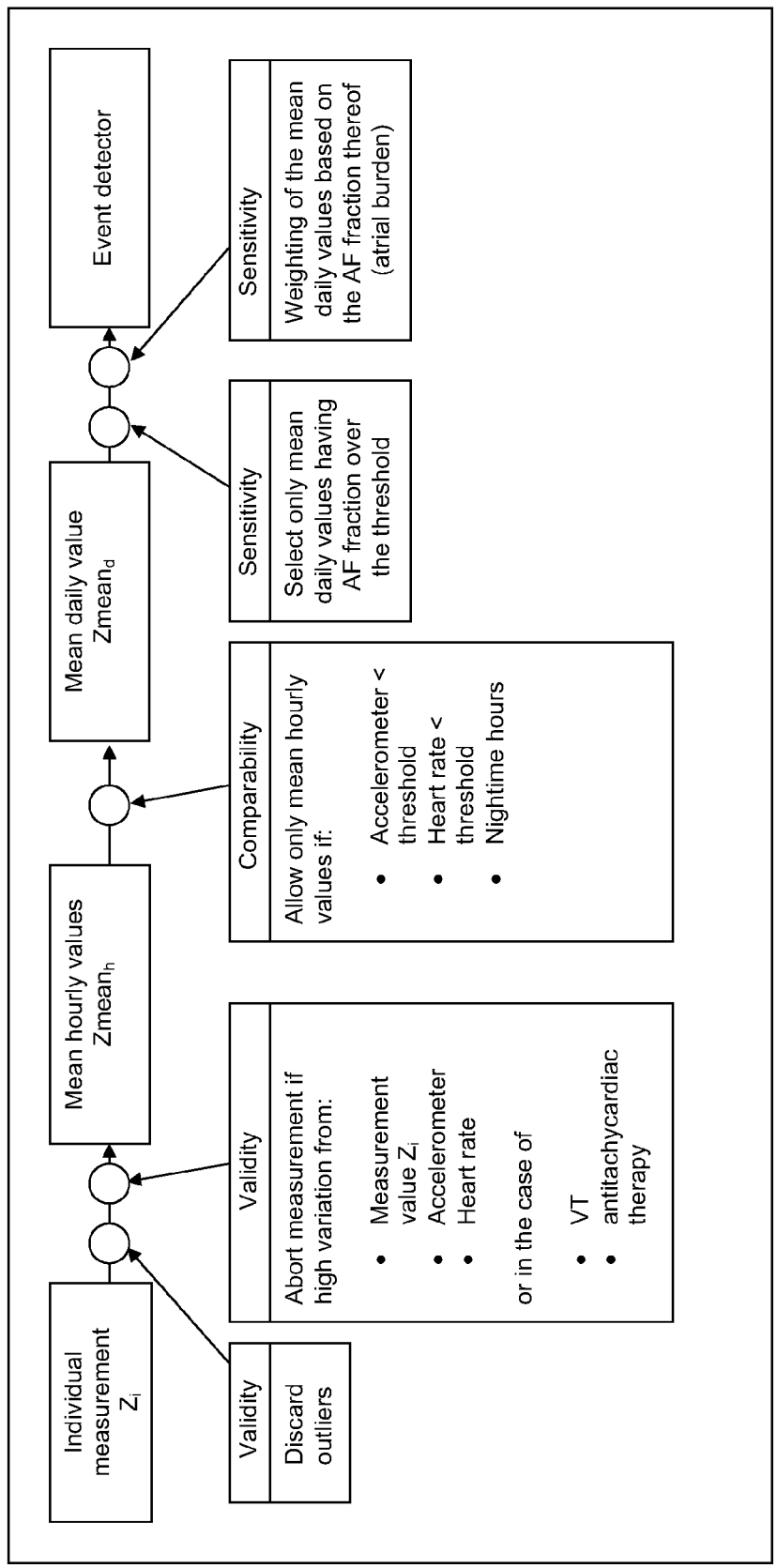
FIG. 10: an example of a high weighting of mean daily values having a large AF fraction.

A third example, which is illustrated in FIG. 10, shows a high weighting of mean daily values having a high AF fraction. For this purpose, first the mean daily values $Zmean_d$ which meet the following conditions (for comparability) are determined from $Zmean_h$:
i. the accelerometer signal is below a threshold (which is to say the patient is at rest)
ii. the heart rate is below a threshold (which is to say the patient is at rest)

Thereafter, the mean daily values $Zmean_d$ are weighted based on the AF fraction thereof on this day (atrial burden A) for further processing. This can be done, for example, using the following rule:

$$P = \sum_i A_i Zmean_{d,i} / \sum_i A_i$$

A fourth example explains the selection of measurements under high physical strain. For this purpose, measurements having an accelerator signal over a certain threshold are selected and are averaged, weighted using the accelerometer signal level thereof, to produce a mean daily value under strain: $Zmean_{d\_Load}$. Here, only the $Zmean_h$ values which meet the following additional conditions are taken into account (for comparability):
i. Heart rate within a predetermined (elevated) range
ii. Measurement during hours of the day (such as 8:00 am-8:00 pm).

A fifth example relates to the selection of measurements at night. For this purpose, measurements are selected at night time (such as 11:00 pm-4:00 am) and averaged to produce a daily mean value $Zmean_{d\_Night}$. Here, only the $Zmean_h$ values which meet the following additional conditions are taken into account (for comparability):
i. Heart rate within a predetermined, low range (such as 40-80 bpm)
ii. Accelerometer signal below a threshold
iii. No AF
iv. Low variance of the respiration parameters (regular breathing)

A sixth example relates to the selection of measurements at a certain daytime. For this purpose, measurements are selected within a daytime range (such as 02:00 pm-05:00 pm) and averaged to produce a daily mean value $Zmean_{d\_Daytime}$. Here, only the $Zmean_h$ values which meet the following additional conditions are taken into account (for comparability):
i. Heart rate within a predetermined, low range (such as 60-90 bpm), which is to say the patient is at rest
ii. Accelerometer signal below a threshold
iii. No AF Of course it is also possible to conduct several such evaluations in parallel and feed them as separate "channels" to the event detector.

The evaluation and processing unit as defined by one or more embodiments of the invention can be embodied by the control unit 54. As an alternative, the evaluation and processing unit can also be part of the service center 130. The evaluation and processing unit can also be part of the impedance evaluation unit 78 (at least in some respects).

Input values of the evaluation and processing unit are the output values of the activity sensor 60 and of the clock 80. Furthermore, the Closed Loop frequency adaptation signal, respiration parameters (from impedance measurements 76, 70), arrhythmia parameters (from CTRL 54), or the position sensor 82 can supply input values. In this way, the weighting of the measurement values can take place as a function of the intensity of a physical activity and/or the time of day, and the like. In addition, the evaluation and processing unit is designed to directly evaluate the measurement values in order to weight them as a function of the evaluation result.

The evaluation and processing unit is designed to weight measurement values of impedance signals captured by way of the impedance capturing and evaluation unit and/or measurement values of intracardiac electrocardiogram signals recorded by the individual sensing units after evaluating the respective signal curve, and optionally while taking the output signals of the position sensor and of the clock into account, and to process them according to the weighting for detecting cardiac decompensation.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A monitoring apparatus comprising:
   a signal input for signals that represent measurement values of one or more physiological parameters; and,
   an evaluation and processing unit connected to the signal input, wherein said evaluation and processing unit is configured to
   select, or give different weightings to, individual values among the measurement values received and selected, or not selected, for further processing according to one or more criteria such that the measurement values and selected measurement values are given a high weighting or a low weighting, depending on whether previously set or adaptive threshold values for measurement values, and/or previously set or adaptive threshold values for changes compared to or deviations from previously recorded measurement values are adhered to, exceeded, or not met, abort an evaluation of the measurement values if a particular measurement value based on a weighting will be below a specified or adaptive threshold, and abort a measurement, or completely eliminate the measurement while conducting the measurement or prior to conducting the measurement respectively, if it is to be expected from the measurement values of other parameters, or from the parts of the measurement already conducted, that the weighting will be below a certain threshold.

2. The monitoring apparatus according to claim 1, wherein the evaluation and processing unit is further configured to repeat a measurement in an event of an aborted evaluation, or an eliminated measurement, within a specified repetition time frame after a first measurement, as soon as the one or more criteria for elimination of the measurement are no longer met.

3. The monitoring apparatus according to claim 1, wherein the evaluation and processing unit is further configured to select, or give different weightings to, the individual values among the measurement values received for further processing according to one or more criteria such that measurement values that raise doubt as to validity thereof are not selected or given a very low weighting, if:

a variability of a measurement value, which is a mean value from many individual values, exceeds a specified particular threshold value, or a sensor signal, that identifies an activity of a patient, comprises any one or more of
  a Closed Loop Stimulation rate control signal,
  accelerometer output value,
  respiratory rate, respiration depth,
  and/or minute volume,
wherein said sensor signal exceeds the specified particular threshold value, or a signal, or several signals, indicate an unstable condition of the patient, such as ventricular tachycardia, or antitachycardiac therapy is being conducted.

4. The monitoring apparatus according to claim 1, wherein the evaluation and processing unit is further configured to select, or give different weightings to, the individual values among the measurement values received for further processing according to one or more criteria such that the measurement values under conditions which enable good comparability are given a high weighting and preferentially evaluated.

5. The monitoring apparatus according to claim 1, wherein the evaluation and processing unit is further configured to give the high weighting to and preferentially evaluate measurement values recorded during a specified time range of the day.

6. The monitoring apparatus according to claim 4, wherein the evaluation and processing unit is further configured to give high weightings to and preferentially evaluate measurement values which are associated with a specified heart rate range, and/or to give the high weightings to and preferentially evaluate measurement values which are associated with a specified mental or physical stress range, and/or give the high weightings to and preferentially evaluate measurement values which accompany a fraction of atrial fibrillation within a certain time period, which is above or below a specified threshold value, and/or give the high weightings to and preferentially evaluate measurement values which accompany a respiratory amplitude and respiratory rate in a predetermined or adaptively determined interval.

7. The monitoring apparatus according to claim 1, wherein the evaluation and processing unit is further configured to select, or give different weightings to, the individual values among the measurement values received for further processing according to one or more criteria such that measurement values obtained under conditions during which a measurement signal exhibits high sensitivity toward an effect to be observed are preferentially evaluated and given a the high weighting.

8. The monitoring apparatus according to claim 7, wherein the evaluation and processing unit is further configured to give high weightings to and preferentially evaluate measurement values which accompany a fraction of atrial fibrillation within a certain time period, which is above a specified threshold, and/or give high weightings to and preferentially evaluate measurement values which are recorded under high physical or mental strain, and/or to give high weightings to and preferentially evaluate measurement values which are recorded within a specified heart rate range.

9. The monitoring apparatus according to claim 7, further comprising an input for a position sensor that indicates a horizontal or vertical position, wherein the evaluation and processing unit is further configured to give high weightings to and preferentially evaluate measurement values recorded in a position that was established beforehand.

10. The monitoring apparatus according to claim 7, further comprising an input for a position sensor signal that indicates a horizontal or vertical position, and another input for a time-of-day-signal wherein the evaluation and processing unit is further configured to give high weightings to and preferentially evaluate measurement values that are recorded during morning, after switching from a horizontal position into a vertical position, or during evening, after switching from a vertical position into a horizontal position.

11. The monitoring apparatus according to claim 1, further comprising:
an impedance capturing unit;
impedance evaluation unit;
wherein the evaluation and processing unit is connected to the impedance capturing unit and impedance evaluation unit;
wherein said impedance capturing unit is configured to determine an impedance signal, which represents an intracardiac impedance curve; and,
wherein said impedance evaluation unit is further configured to determine an activity signal that indicates high physical strain from a time curve of the impedance signal.

12. The monitoring apparatus according to claim 1, wherein the evaluation and processing unit is further configured to process the measurement values of one or more of the following parameters: biomarkers, electrolytes, glucose, hematocrit, blood resistivity, temperature and/or outside pressure.

13. The monitoring apparatus according to claim 1, further comprising an impedance capturing unit, wherein the impedance capturing unit and the evaluation and processing unit are integrated in an implant, or the impedance capturing unit is integrated in the implant and the evaluation and processing unit is integrated in an external device that communicates with the implant, or the impedance capturing unit is integrated in the implant and the evaluation and processing unit is integrated in a service center communicating indirectly with the implant.

14. A method for processing measurement values of physiological parameters using a monitoring apparatus comprising a signal input for signals that represent measurement values of one or more physiological parameters and an evaluation and processing unit connected to the signal input, wherein the method for processing measurement values using said evaluation and processing unit comprises:

- selecting, or giving different weightings to, individual values among the measurement values received and selected, or not selected, for further processing according to one or more criteria such that the measurement values and selected measurement values are given a high weighting or a low weighting, depending on whether previously set or adaptive threshold values for measurement values, and/or previously set or adaptive threshold values for changes compared to or deviations from previously recorded measurement values are adhered to, exceeded, or not met,
- aborting an evaluation of the measurement values if a particular measurement value based on a weighting will be below a specified or adaptive threshold, and
- aborting a measurement, or completely eliminating the measurement while conducting the measurement or prior to conducting the measurement respectively, if it is to be expected from the measurement values of other parameters, or from the parts of the measurement already conducted, that the weighting will be below a certain threshold.

15. The method for processing measurement values of physiological parameters using a monitoring apparatus according to claim 14, further comprising:

- selecting, or giving different weightings to, the individual values among the measurement values received for further processing according to one or more criteria such that measurement values that raise doubt as to validity thereof are not selected or given a very low weighting, if:
  - a variability of a measurement value, which is a mean value from many individual values, exceeds a specified particular threshold value, or
  - a sensor signal, that identifies an activity of a patient, comprises any one or more of
    - a Closed Loop Stimulation rate control signal,
    - accelerometer output value,
    - respiratory rate, respiration depth,
    - and/or minute volume,
  - wherein said sensor signal exceeds the specified particular threshold value, or
  - a signal, or several signals, indicate an unstable condition of the patient, such as ventricular tachycardia, or antitachycardiac therapy is being conducted.

* * * * *